United States Patent [19]

Usami et al.

[11] Patent Number: 5,249,453
[45] Date of Patent: Oct. 5, 1993

[54] METHOD OF COMPENSATING OUTPUT OF A/F RATIO SENSOR

[75] Inventors: Jun Usami, Aichi; Motohiro Nishiwaki, Nagoya, both of Japan

[73] Assignee: NGK Insulators, Ltd., Japan

[21] Appl. No.: 801,380

[22] Filed: Dec. 2, 1991

[30] Foreign Application Priority Data

Nov. 30, 1990 [JP] Japan ................... 2-337836

[51] Int. Cl.$^5$ .......................................... G01N 31/00
[52] U.S. Cl. .................................. 73/23.32; 204/408
[58] Field of Search .............. 73/23.32, 116; 204/408, 204/421

[56] References Cited

U.S. PATENT DOCUMENTS

| | | | |
|---|---|---|---|
| 4,337,745 | 7/1982 | Pomerantz | 123/440 |
| 4,413,601 | 11/1983 | Matsuoka et al. | 123/480 |
| 4,472,262 | 9/1984 | Kondo et al. | 204/408 |
| 4,782,690 | 11/1988 | Terasaka | 73/116 |
| 4,875,990 | 10/1989 | Kodachi et al. | 204/408 |
| 4,958,611 | 9/1990 | Uchinami et al. | 123/479 |

FOREIGN PATENT DOCUMENTS

| | | |
|---|---|---|
| 0170428 | 2/1986 | European Pat. Off. |
| 62-104152 | 7/1987 | Japan |
| 62-238455 | 10/1987 | Japan |
| 62-257056 | 11/1987 | Japan |
| 62-274255 | 11/1987 | Japan |
| 1218737 | 1/1971 | United Kingdom ............... 204/408 |

OTHER PUBLICATIONS

Patent Abstracts of Japan vol. 013, No. 405 (M-868) Sep. 7, 1989 & JP-A-1147140 (Mitsubishi Electric Corp) Jun. 8, 1989.

Patent Abstracts of Japan vol. 013, No. 405 (M-868) Sep. 7, 1989 & JP-A-114739 (Mitsubishi Electric Corp) Jun. 8, 1989.

*Primary Examiner*—Jerry W. Myracle
*Attorney, Agent, or Firm*—Parkhurst, Wendel & Rossi

[57] ABSTRACT

A method of compensating an output of a sensor adapted to determine an air/fuel ratio of an air-fuel mixture, depending upon an oxygen concentration of an exhaust gas produced as a result of combustion of the air-fuel mixture, wherein the sensor includes a sensing element which has at least one electrochemical cell each having an oxygen-conductive solid electrolyte body and at least one pair of electrodes The method includes the steps of detecting at least one parameter selected from the group consisting of a temperature Tc of the sensing element, a pressure Pg of the exhaust gas, and a temperature Tg of the exhaust gas, and adjusting the output $y_0$ of the sensor, based on the at least one parameter detected, to obtain a compensating output of the sensor.

6 Claims, 5 Drawing Sheets

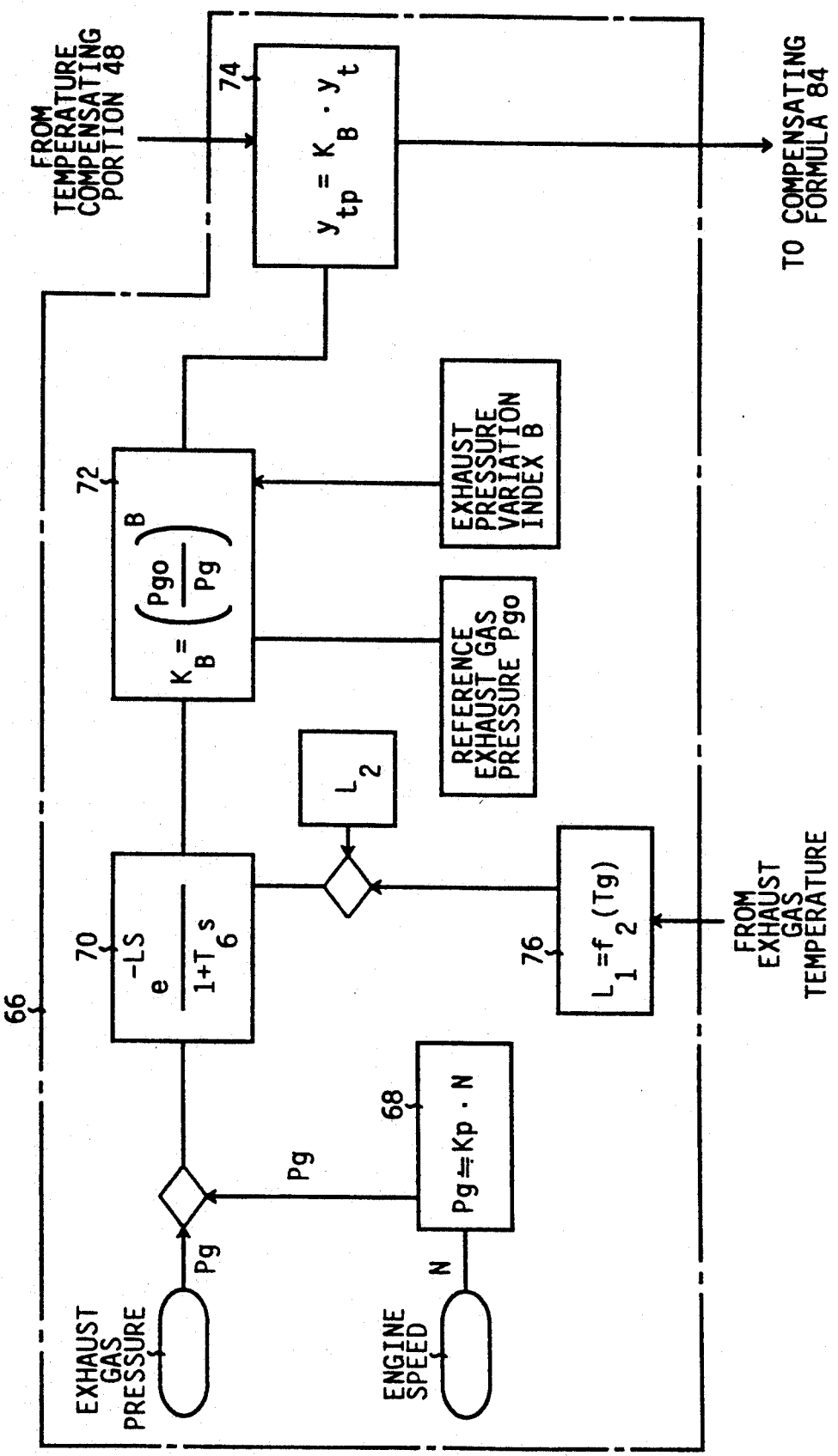

METHOD OF COMPENSATING OUTPUT OF A/F RATIO SENSOR

BACKGROUND OF THE INVENTION

1. Field of the Invention

The present invention relates generally to a method of compensating the output of an air/fuel ratio sensor, and more particularly, to such a compensating method suitably applicable to a control system associated with a sensor which is adapted to measure an excess or shortage amount of oxygen in an exhaust gas emitted from an internal combustion engine of a motor vehicle or from an industrial furnace, to thereby determine an air/fuel ratio of an air-fuel mixture which produces the exhaust gas. The invention is concerned with such a sensor output compensating method that assures improved accuracy of determination of the air/fuel ratio of the air-fuel mixture.

2. Discussion of the Prior Art

In the art of measuring the air/fuel ratio of an air-fuel mixture supplied to an automotive internal combustion engine or an industrial furnace, it is generally practiced to measure the concentrations of the components (e.g., $O_2$, $CO_2$, CO, $H_2$ and HC) of the exhaust gas produced as a result of combustion of the air-fuel mixture, for calculating or determining the air/fuel ratio of the mixture based on the measured concentrations. For measuring the concentration of $O_2$ in the exhaust gas, there has been widely used an air/fuel ratio sensor in the form of an electrochemical sensing element of a so-called single-cell type which is operated according to the principle of an oxygen concentration cell. In recent years, there is available a so-called double-cell type air/fuel ratio sensor which includes an electrochemical cell operated according to the principle of the oxygen concentration cell, and another electrochemical cell adapted for performing an oxygen pumping action. This double-cell type sensor is advantageous for its improved accuracy of determination of the air/fuel ratio (A/F ratio) of the air-fuel mixture, based on a known relationship between the concentrations of the components of the exhaust gas produced by the combustion of the air-fuel mixture, and the output value of the sensor (more precisely, the oxygen pumping current applied to the pumping cell).

The double-cell type electrochemical sensor has a sensing element which includes two electrochemical cells each having at least one pair of electrodes disposed on an oxygen-ion conductive solid electrolyte body. The sensing element has an internal space formed between the two cells so that an exhaust gas under examination is introduced under a predetermined diffusion resistance. The first electrochemical cell (referred to as "sensing cell"), which is operated according to the principle of an oxygen concentration cell, produces an electromotive force induced according to the Nernst equation, depending upon the oxygen partial pressure in the atmosphere in the internal space. On the other hand, the second electrochemical cell (referred to as "pumping cell") is operated to perform an oxygen pumping action to change the oxygen partial pressure in the internal space so that the electromotive force coincides with a level which corresponds to an excess oxygen ratio or excess air ratio ($\lambda$) of 1 ($\lambda = 1$). The pumping current applied to the pumping cell to establish the excess oxygen ratio of 1 is used as the output of the air/fuel ratio sensor, which varies with the components of the exhaust gas.

In the single-cell type air/fuel ratio sensor indicated above, the output E (electromotive force) changes with the oxygen partial pressure of the exhaust gas, according to the following Nernst equation (i):

$$E = \frac{RTc}{nF} \cdot \log\left(\frac{P_{O_2}(I)}{P_{O_2}(II)}\right) \quad \text{(i)}$$

where,
- E: electromotive force of A/F ratio sensor (sensing element thereof),
- R: gas constant (Gas-law constant),
- Tc: temperature of the sensing element
- n: number of ions,
- F: Faraday constant (faraday),
- $P_{O_2}(I)$: oxygen partial pressure of reference gas,
- $P_{O_2}(II)$: oxygen partial pressure of exhaust gas.

In the double-cell type air/fuel ratio sensor (which may be a type in which the sign of the voltage applied to the pumping cell is reversed depending upon the output of a $TiO_2$ sensor adapted to determine whether the air/fuel mixture which produces the exhaust gas is a fuel-lean mixture or a fuel-rich mixture), the output Ip (pumping current) changes with the partial pressures of $O_2$, CO and $H_2$ of the exhaust gas, according to the following equation (ii):

$$Ip = K_{O_2} \cdot P_{O_2}(II) - K_{co} \cdot P_{co} - K_{H_2} \cdot P_{H_2} \quad \text{(ii)}$$

where,
- $K_{O_2}$: Current sensitivity coefficient of oxygen concentration,
- $P_{O_2}(II)$: $O_2$ partial pressure of exhaust gas,
- $K_{co}$: Current sensitivity coefficient of CO concentration,
- $P_{co}$: Co partial pressure of exhaust gas,
- $K_{H_2}$: Current sensitivity coefficient of H, concentration, and
- $P_{H_2}$: $H_2$ partial pressure of exhaust gas.

The components of the exhaust gas are obtained by comparison of reaction molar numbers before and after the combustion of the air-fuel mixture, as indicated by the following equations (iii-1) and (iii-2):

a) Before combustion $$C_mH_n + \lambda\{O_2 + (m+n/4).(79.05/20.95).N_2\} \quad \text{(iii-1)}$$

After combustion $$A_1.CO + A_2.CO_2 + A_3.H_2 + A_4.H_2O + A_5.O_2 + A_6.N_2 \quad \text{(iii-2)}$$

where,
- $C_mH_n$: Carbon/hydrogen fuel
- m: molar number of carbon component in 1 mole of the fuel,
- n: molar number of hydrogen component in 1 mole of the fuel,
- $\lambda$: excess air ratio,
- $A_1 \sim A_6$: molar numbers of the relevant components of the exhaust gas, the values $A_1.CO$ and $A_3.H_2$ being approximately 0% where $\lambda > 1$, while the values $A_1.CO$ and $A_3.H_2$ being not 0% where $\lambda < 1$.

Therefore, the relationship between the sensor output, and the oxygen concentration of the exhaust gas, or the excess air ratio or A/F ratio of the air-fuel mixture can be obtained directly by experiments, or by approximating calculation, by using in the above equations (iii-1) and (iii-2) a water gas reaction coefficient K(t) represented by the following equation (iv):

$$K(t) = \frac{P_{co} \cdot P_{H_2O}}{P_{co_2} \cdot P_{H_2}} \quad \text{(iv)}$$

where,
- $P_{co}$: CO partial pressure of exhaust gas,
- $P_{H_2O}$: H₂O partial pressure of exhaust gas,
- $P_{CO_2}$: CO₂ partial pressure of exhaust gas, and
- $P_{H_2}$: H₂ partial pressure of exhaust gas. In the single-cell type air/fuel ratio sensor designed to determine the A/F ratio of the air-fuel mixture based on its output, the value of the output is influenced by a variation in the temperature of the electrochemical sensing element and the pressure of the exhaust gas, as is understood from the Nernst equation, whereby the variation of the temperature and pressure results in an error in the A/F ratio as determined based on the output value, even if the oxygen partial pressure of the exhaust gas is constant. This phenomenon is theoretically apparent. In the known sensor, the error in the sensor output due to the variations in the temperature of the sensing element, pressure of the exhaust gas and other parameters is inevitable or unavoidable. At present, there is no such single-cell type A/F ratio sensors that are capable of dealing with the exhaust gas which is produced as a result of a fuel-rich air-fuel mixture whose A/F ratio is lower than the stoichiometric point.

On the other hand, the double-cell type A/F ratio sensor is capable of determining the A/F ratio of the air-fuel mixture even where the A/F ratio changes from a fuel-lean range to a fuel-rich range, across the stoichiometric point. For this reason, the double-cell type A/F ratio sensor is increasingly used. However, it is recognized that this double-cell type A/F ratio sensor also suffers from an error in the output value or the A/F ratio determined, due to the variations in the temperature of the sensing element (sensing and pumping cells) and the temperature and pressure of the exhaust gas.

Up to the present, no effective methods are available for compensating the sensor output for the variations in the sensor temperature and the exhaust gas temperature and pressure. Namely, these fluctuating parameters have been treated as being constant, in determining the A/F ratio of the air-fuel mixture, whereby the resulting error has been inevitable.

In the light of the above drawbacks experienced in the prior art, there is a long-felt need for improving the accuracy of measurement or determination of the A/F ratio, in particular, in view of the recent growing requirements for more stringent regulation of the exhaust emission from an automotive internal combustion engine, and for further enhancement of the fuel economy of the vehicle.

SUMMARY OF THE INVENTION

It is therefore an object of the present invention to provide a method of compensating an output of an A/F ratio sensor, for variations in the temperature of the sensing element, and/or pressure and/or temperature of the exhaust gas to be dealt with, so as to improve the accuracy of determination or measurement of the A/F ratio of the air-fuel mixture which produces the exhaust gas.

The above object may be achieved according to the principle of the present invention, which provides a method of compensating an output of a sensor adapted to determine an air/fuel ratio of an air-fuel mixture, depending upon an oxygen concentration of an exhaust gas produced as a result of combustion of the air-fuel mixture, the sensor including a sensing element which has at least one electrochemical cell each having an oxygen-conductive solid electrolyte body and at least one pair of electrodes, the method comprising the steps of: detecting at least one parameter selected from the group consisting of a temperature Tc of the sensing element, a pressure Pg of the exhaust gas, and a temperature Tg of the exhaust gas; and adjusting the output $y_0$ of the sensor, based on the at least one parameter detected, to obtain a compensating output of the sensor.

According to the method of the present invention, the output of the air/fuel ratio sensor is suitably compensated for variations in the temperature of the sensing element, and/or the temperature and/or pressure of the exhaust gas, which variations are not conventionally taken into account in determining the air/fuel ratio of the air-fuel mixture based on the sensor output. The instant compensating method is effective to easily and accurately control the system of determining the A/F ratio, for improved accuracy of determination of the A/F ratio based on the compensated output value of the sensor, thereby assuring accurate control of the A/F ratio of the air-fuel mixture to be supplied to an automotive internal combustion engine or industrial furnace.

According to one feature of the present invention, the step of detecting at least one parameter consists of detecting the temperature Tc of the sensing element, and the step of adjusting the output $y_0$ of the sensor consists of adjusting the output $y_0$, according to the following formulas (1—1) and (1-2), to obtain a compensated output $y_l$ of the sensor:

$$y_l = y_0 \times K_A \quad (1—1)$$

$$K_A = (Tco/Tc)^A \quad (1\text{-}2)$$

where,
- $T_{Co}$: reference temperature of the sensing element, and
- A: temperature variation index measured at the sensing element.

According to another feature of the invention, the sensing element has a first and a second electrochemical cell and an internal space formed therebetween, the first electrochemical cell being operable according to the principle of an oxygen concentration cell, so as to produce an electromotive force corresponding to an oxygen partial pressure of an atmosphere in the internal space into which the exhaust gas diffuses with a predetermined diffusion resistance, the second electrochemical cell operating to perform an oxygen pumping action to adjust the oxygen partial pressure in the internal space so that the electromotive force substantially coincides with a constant value, the output of the sensor being obtained as a pumping current applied to the second electrochemical cell. According to this feature of the invention, the step of detecting at least one parameter consists of detecting the pressure Pg of the exhaust gas, and the step of adjusting the output $y_0$ of the sensor consists of adjusting the output $y_0$, according to the following formulas (2A-1) and (2A-2), to obtain a compensated output $y_p$ of the sensor:

$$y_p = y_0 \times K_B \quad (2A\text{-}1)$$

$$K_B = (P_{g0}/P_g)^B \quad (2A\text{-}2)$$

where,
 $P_{g0}$: reference pressure of the exhaust gas, and
 B: variation index of the exhaust gas pressure measured for the sensing element.

According to a further feature of this invention, the sensing element consists of a single electrochemical cell, and the output of the sensor is obtained as an electromotive force induced by the single electrochemical cell. In this case, the step of detecting at least one parameter consists of detecting the pressure $y_p$ of the exhaust gas, and the step of adjusting the output $y_0$ of the sensor consists of adjusting the output $y_0$, according to the following formulas (2B-1) and (2B-2), to obtain a compensated output $y_p$ of the sensor:

$$y_p = y_0 - K_B \quad (2B\text{-}1)$$

$$K_{B'} = \left(\frac{RT_c}{4F}\right) \cdot \log(P_{g0}/P_g) \quad (2B\text{-}2)$$

where,
 R: gas constant,
 F: Faraday constant, and
 $P_{g0}$: reference pressure of the exhaust gas.

According to a still further aspect of the instant invention, the sensing element has a first and a second electrochemical cell and an internal space formed therebetween, the first electrochemical cell being operable according to the principle of an oxygen concentration cell, so as to produce an electromotive force corresponding to an oxygen partial pressure of an atmosphere in the internal space into which the exhaust gas diffuses with a predetermined diffusion resistance, the second electrochemical cell operating to perform an oxygen pumping action to adjust the oxygen partial pressure in the internal space so that the electromotive force substantially coincides with a constant value, the output of the sensor (40) being obtained as a pumping current applied to the second electrochemical cell. According to this feature of the invention, the step of detecting at least one parameter consists of detecting the temperature Tc of the sensing element and the pressure Pg of the exhaust gas, and the step of adjusting the output $y_0$ of the sensor consists of adjusting the output $y_0$, according to the following formulas (3A-1), (3A-2) and (3A-3), to obtain a compensated output $y_{tp}$ of the sensor:

$$y_{tp} = y_0 \times K_A \times K_B \quad (3A\text{-}1)$$

$$K_A = (T_{c0}/T_c)^A \quad (3A\text{-}2)$$

$$K_B = (P_{g0}/P_g)^B \quad (3A\text{-}3)$$

where, $T_{c0}$: reference temperature of the A/F sensing element,
 A: temperature variation index measured at the sensing element,
 $P_{g0}$: reference pressure of the exhaust gas, and
 B: pressure variation index measured at the sensing element.

According to a yet further feature of the present invention, the sensing element consists of a single electrochemical cell, and the output of the sensor is obtained as an electromotive force induced by the single electrochemical cell, and wherein the step of detecting at least one parameter consists of detecting the temperature Tc of the sensing element and the pressure $y_p$ of the exhaust gas, and the step of adjusting the output $y_0$ of the sensor consists of adjusting the output $y_0$, according to the following formulas (3B-1), (3B-2) and (3B-3), to obtain a compensated output $y_{tp}$ of the sensor:

$$y_{tp} = (y_0 - K_{B'}) \cdot K_A \quad (3B\text{-}1)$$

$$K_A = (T_{c0}/T_c)^A \quad (3B\text{-}2)$$

$$K_{B'} = \left(\frac{RT_c}{4F}\right) \cdot \log(P_{g0}/P_g) \quad (3B\text{-}3)$$

where,
 A: temperature variation index (=1) of the sensing element,
 $T_{c0}$: reference temperature of the sensing element,
 R: gas constant,
 F: Faraday constant, and
 $P_{g0}$: reference pressure of the exhaust gas.

According to another feature of the invention, the method further comprises a determining step of determining whether or not the output of the sensor represents the air/fuel ratio lower than a stoichiometric point, and the step of detecting at least one parameter consists of detecting the temperature Tg of the exhaust gas if an affirmative decision is obtained in the determining step, while the step of adjusting the output of the sensor consists of calculating by approximation an equilibrium temperature $T_H$ of an water gas which gives an equilibrium of reaction of the exhaust gas, based on the temperature Tg of the exhaust gas, according to an experimentally obtained approximating formula, and compensating the output of the sensor so as to establish the equilibrium of reaction of the water gas at the equilibrium temperature $T_H$.

DETAILED DESCRIPTION OF THE INVENTION

The present invention was developed and perfected as a result of extensive studies and investigations and various experiments on undesirable influences on the output values of A/F ratio sensors, of the variations in the temperature of the sensing element and/or the pressure and/or temperature of the exhaust gas to be measured by the sensor.

Firstly, the influences of the temperature of the sensing element and the pressure of the exhaust gas on the output of a double-cell type A/F ratio sensor were considered. In the double-cell type, the output is obtained in the form of a pumping current Ip which is expressed by the above equation (ii), wherein $K_{O2}$, $K_{CO}$, and $K_{H2}$, are current sensitivity coefficients of $O_2$, CO and $H_2$, respectively. These coefficients are determined by the configuration of the A/F ratio sensor (more precisely, configuration and dimensions of the internal space), and the mode of diffusion of the individual components $O_2$, CO and $H_2$ through the internal space (e.g., thin flat space) formed in the sensing element. Described in detail, the Knudsen diffusion of the exhaust gas occurs if the thickness of the internal thin flat space is 100 angstroms or less, while the bulk diffusion occurs if the thickness is relatively large. In the Knudsen diffusion, the diffusion constant Dk is in direct proportion to Tc (temperature Tc of the sensing element) to the power ½. In the bulk diffusion, the diffusion constant Db is in direct proportion to Tc to the power ⅔ and in inverse proportion to Pg (pressure of the exhaust gas). The resultant diffusion constant D of these constants Dk and Db is represented by the following equation (v):

$$\frac{1}{D} = \frac{l}{Dk} + \frac{1-l}{Db} \qquad \text{(v)}$$

where,
l: ratio of Knudsen diffusion amount to the total diffusion amount.

On the other hand, a relationship between the polarographic oxygen pumping current Ip and the partial pressure Pg of the component is represented by the following equation (vi):

$$Ip = D \cdot \frac{M}{L} \cdot Pg \cdot C \qquad \text{(vi)}$$

where,
M: gas diffusion cross sectional area of the sensing element of the A/F ratio sensor,
L: gas diffusion length through the sensing element, and
C: molar concentration of the component.

It was found from the above analysis that the output value (Ip) of the double-cell type A/F ratio sensor changes in a certain relationship with not only the temperature of the sensing element, but also the pressure of the exhaust gas.

Various experiments were conducted by the applicants, in an attempt to find out the relationship between a variation in the temperature Tc of the sensing element and a variation in the output Ip of the double-cell type sensor. A careful study on the results of the experiments revealed that the relationship between the variations in the parameters Tc and Ip can be approximated by the following equation (vii):

$$\frac{Ip}{Ipo} \approx \left(\frac{Tc}{Tco}\right)^A \qquad \text{(vii)}$$

where,
Tco: reference temperature of the sensing element,
Ipo: output of the sensor at Tco,
A: temperature variation index measured at the sensing element TABLE 1 indicates a result of an exemplary experiment in which the output values Ip of the sensor at different temperature values Tc of the sensing elements were actually measured. The table also shows the sensor output values Ip' which are calculated according to the equation indicated at the bottom of the table, which corresponds to the above equation (vii) The experiment was conducted in the atmosphere.

Based on the experimental result indicated by the above equation (vii), there were obtained the above formulas (1—1) and (1-2) for compensating the sensor output for a variation in the temperature Tc of the sensing element of the sensor.

Further, various experiments were conducted by the applicants, in an attempt to find out the relationship between a variation in the pressure Pg of the exhaust gas and a variation in the output Ip of the double-cell type sensor. A careful study on the results of the experiments revealed that the relationship between the variations in the parameters Pg and Ip can be approximated by the following equation (viii):

$$\frac{Ip}{Ipo} \approx \left(\frac{Pg}{Pgo}\right)^B \qquad \text{(viii)}$$

Pgo: reference pressure of the exhaust gas,
Ipo: output of the sensor at Pgo, and
B variation index of the exhaust gas pressure measured for the sensing element.

TABLE 1

| Gas Temp. | Sensing Element Temp. Tc | | Measured Output Ip | Calculated Output Ip' |
|---|---|---|---|---|
| (°C.) | (°C.) | (°K.) | (mA) | (mA) |
| 22 | 778 | 1051.2 | 7.345 | 7.345 |
| 300 | 784 | 1057.2 | 7.365 | 7.365 |
| 600 | 796 | 1069.2 | 7.405 | 7.4051 |
| 900 | 938 | 1211.2 | 7.860 | 7.8618 |

Equation used to calculate the output Ip':

$$\frac{Ip}{Ipo} \approx \left(\frac{Tc}{Tco}\right)^{0.48}$$

TABLE 2 indicates a result of an exemplary experiment in which the output values Ip of the sensor at different pressure levels Pgo of the exhaust gas were actually measured. The table also shows the sensor output values Ip' which are calculated according to the equation indicated at the bottom of the table, which corresponds to the above equation (viii). The experiment was conducted in the atmosphere.

Based on the experimental result indicated by the above equation (viii), there were obtained the above formulas (2A-1) and (2A-2) for compensating the output Ip of the sensor for a variation in the pressure Pgo of the exhaust gas.

TABLE 2

| Gas pressure Pgo (mm Hg) | Measured Output Ip (mA) | Calculated Output Ip' (mA) |
|---|---|---|
| 660 | 6.837 | 6.8350 |
| 760 | 7.345 | 7.3450 |
| 860 | 7.824 | 7.8229 |
| 1000 | 8.449 | 8.4484 |
| 1210 | 9.310 | 9.3110 |

Equation used to calculate the output Ip':

$$\frac{Ip}{Ipo} \approx \left(\frac{Pg}{Pgo}\right)^{0.51}$$

It was also found that the relationship between the sensor output Ip and the variations in the temperature Tc of the sensing element and the pressure Pg of the exhaust gas can be approximated by the following equation (ix), which is obtained by combining the above equations (vii) and (viii):

$$\frac{Ip}{Ipo} \approx \left(\frac{Tc}{Tco}\right)^A \cdot \left(\frac{Pg}{Pgo}\right)^B \quad \text{(ix)}$$

Tco: reference temperature of the sensing element,
Pgo: reference pressure of the exhaust gas,
Ipo: sensor output at Tco and Pgo,
A: temperature variation index measured at the sensing element, and
b: variation index of the exhaust gas pressure measured for the sensing element.

Based on the result indicated by the above equation (ix), there were obtained the formulas (3A-1), (3A-2) and (3A-3) for compensating the sensor output Ip for the variations in the temperature of the sensing element and the pressure of the exhaust gas.

In the single-cell type A/F ratio sensor, on the other hand, the output $E_0$ (electromotive force) of the sensor is produced according to the Nernst equation, namely, equation (i) indicated above. It will therefore be understood that the output $E_0$ will change with a variation in the temperature Tc of the sensing element.

The output of the single-cell type A/F ratio sensor can be compensated for the temperature variation of the sensing element, according to the formulas (1—1) and (1-2) used for the double-cell type sensor. In this case, however, the temperature variation index A in these formulas is equal to "1" as is apparent from the Nernst equation (i).

There will next be described the manner of compensating the output of the single-cell type A/F ratio sensor for a variation in the pressure of the exhaust gas.

The Nernst equation (i) representing the output $E_0$ of the single-cell type sensor may be converted into the following equation, since the partial $O_2$ pressure $Po_2$(I) of the reference gas is a product $Pgo \times Co_2$(I) of the overall pressure Pgo of the reference gas and the oxygen concentration $Co_2$(I) of the reference gas, while the partial of the exhaust gas is a product $Pg \times Co_2$(II) of the overall pressure Pg of the exhaust gas (gas to be measured) and the oxygen concentration $Co_2$(II) of the exhaust gas:

$$E_0 = \frac{RTc}{4F} \cdot \log\left(\frac{Pgo \cdot Co_2(I)}{Pg \cdot Co_2(II)}\right)$$

$$= \frac{RTc}{4F} \cdot \log\left(\frac{Pgo \cdot Co_2(I)}{Pgo \cdot Co_2(II)} \cdot \frac{Pgo}{Pg}\right)$$

Therefore, the Nernst equation (i) may be transformed in to the following equation (x):

$$E_0 = \frac{RTc}{4F} \cdot \log\left(\frac{Pgo \cdot Co_2(I)}{Pgo \cdot Co_2(II)}\right) + \frac{RTc}{4F} \cdot \log\left(\frac{Pgo}{Pg}\right) \quad \text{(x)}$$

$$\frac{RTc}{4F} \cdot \log\left(\frac{Pgo \cdot Co_2(I)}{Pgo \cdot Co_2(II)}\right) = E_0 - \frac{RTc}{4F} \cdot \log\left(\frac{Pgo}{Pg}\right)$$

The left member in the above equation (x) represents the sensor output (E) which is free of an influence by the variation in the pressure Pg of the exhaust gas. Thus, the relationship between the variation in the pressure Pg and the sensor output (E) was found out.

Based on the result indicated by the above equation (x), there were obtained the above formulas (2B-1) and (2B-2) for compensating the sensor output for the variation in the pressure Pg of the exhaust gas.

By multiplying the left and right members of the equation (x) by (Tco/Tc), the following equation (xi) can be obtained:

$$\frac{RTco}{4F} \cdot \log\left(\frac{Pgo \cdot Co_2(I)}{Pgo \cdot Co_2(II)}\right) = \left\{E_0 - \frac{RTc}{4F} \cdot \log\left(\frac{Pgo}{Pg}\right)\right\} \cdot \frac{Tco}{Tc} \quad \text{(xi)}$$

In the thus obtained equation (xi), the left member represents the sensor output (E) which is free of an influence by the variations in the temperature Tc of the sensing element and the pressure Pg of the exhaust gas. Thus, the relationship between the sensor output (E) and the variations in the parameters Tc and Pg was found out.

Based on the result indicated by the above equation (xi), there were obtained the formulas (3A-1), (3A-2) and (3A-3) for compensating the sensor output for the variations in the temperature of the sensing element and the pressure of the exhaust gas.

The water gas reaction coefficient K(t) represented by the above equation (iv) used in calculating the oxygen concentration of the exhaust gas from the sensor output changes with the equilibrium temperature of the water gas reaction. Consequently, the sensor output certainly includes a considerable degree of error according to the conventional system in which the variation in the equilibrium temperature of the water gas reaction is ignored. The amount of this error is particularly large where the temperature of the exhaust gas varies by several hundreds of °C., as in the case of the exhaust gas emitted from an internal combustion engine.

To assure accurate determination of the A/F ratio of the air-fuel mixture, therefore, it is desirable that the sensor output is free of the error or influence caused by the variation in the temperature of the exhaust gas.

The applicants' study and examination of the results of the experiments indicated that the sensor output can be compensated so as to establish an equilibrium of reaction of a water gas at the equilibrium temperature, can be calculated by approximation based on the temperature of the exhaust gas. This compensation permits accurate determination of the A/F ratio, irrespective of a variation in the equilibrium temperature of the water gas reaction.

It is noted that while HC in the exhaust gas has various components, the experiments revealed that the exhaust gas produced as a result of combustion of a fuel-lean or air-rich air-fuel mixture (whose A/F ratio is higher than the stoichiometric point) consists substantially of CO, $CO_2$, $H_2$, $H_2O$, $O_2$ and $N_2$, since even $CH_2$ which can be burnt out with most difficulty among the HC compounds can be burnt out in the vicinity of the electrodes of the sensing element of the A/F ratio sensor.

Consequently, the hydrogen and carbon molecules contained in the exhaust gas produced from a fuel-lean air-fuel mixture react with oxygen, with a result of forming molecules of $CO_2$ and $H_2O$, whereby there arises no water gas reaction. In this respect, the compensation of the sensor output for a variation in the equilibrium temperature of the water gas reaction is not essential.

BRIEF DESCRIPTION OF THE DRAWINGS

The above and optional objects, features and advantages of the present invention will be better understood by reading the following detailed description of a presently preferred embodiment of the invention, when considered in connection with the accompanying drawings, in which:

FIGS. 2A, 2B, 2C and 2D are schematic block diagrams illustrating a compensating routine implemented according to the method.

DETAILED DESCRIPTION OF THE PREFERRED EMBODIMENT

Figure 1:
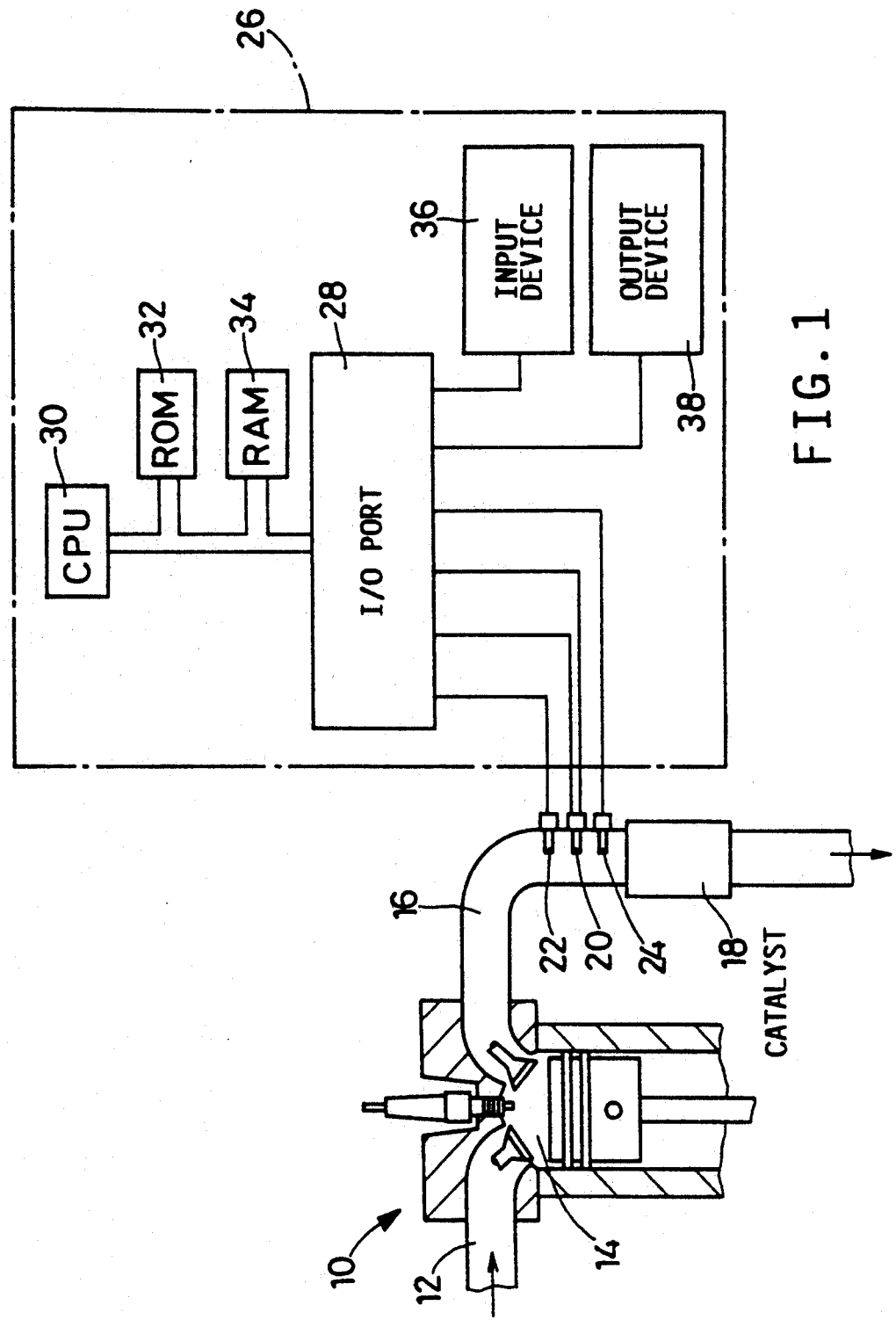
FIG. 1 is a schematic view showing an apparatus for practicing a method of the present invention for compensating the output of a double-cell type oxygen sensor used as a sensor for determining an air/fuel ratio of an air-fuel mixture.

Referring first to FIG. 1, there is shown a system for controlling the air/fuel ratio (A/F ratio) of an air-fuel mixture to be supplied to an internal combustion engine 10 for an automotive vehicle. The system includes a control apparatus 26 adapted to detect the oxygen concentration of the exhaust gas emitted as a result of combustion of the air-fuel mixture, for determining the A/F ratio of the air-fuel mixture, to thereby control the A/F ratio at an optimum level. The system uses, as an A/F ratio sensor, an oxygen sensor indicated generally at 40 in FIG. 2A, which includes a double-cell type A/F sensing element 20. The control apparatus 26 incorporates a data processing arrangement for compensating the output of the oxygen sensor 40 in a manner according to one embodiment of the present invention, which is schematically illustrated in Figs. 2A-2D. The schematic views of FIGS. 2A-2D show various elements for performing respective functions, which will be described.

The internal combustion engine 10 is supplied with the air-fuel mixture through an intake manifold 12. The mixture sucked into a cylinder 14 of the engine 10 is combusted, and an exhaust gas produced as a result of the combustion of the mixture is discharged from the engine 10 through a exhaust pipe 16. The exhaust pipe 16 is equipped with a catalyst 18 for purifying the exhaust gas emission. To a portion of the exhaust pipe 16 between the cylinder 14 and the catalyst 18, there are attached the A/F sensing element 20, a pressure sensing element 22 and a temperature sensing element 24. Output signals generated from these elements 20, 22, 24 are received by an input/output port (I/0 port) 28 of the control apparatus 26.

The control apparatus 26 is a so-called microcomputer which incorporates a central processing unit (CPU) 30, a read-only memory (ROM) 32, a random-access memory (RAM) 34, an input device 36 and an output device 38. The CPU 30 processes input signals according to control programs stored in the ROM 32, while utilizing data storage function of the RAM 34, so that the output of the sensor 40 representative of the A/F ratio of the air-fuel mixture supplied to the engine 10 is fed through the output device 38 to a suitable device for adjusting the A/F ratio of the mixture to be supplied.

Referring next to FIGS. 2A-2D, there will be described the manner of compensating the output of the A/F ratio sensor 40 in the system of FIG. 1. As is known in the prior art, the sensing element 20 of the A/F ratio sensor 40 includes a sensing cell 42 adapted to produce an electromotive force Vs depending upon the oxygen concentration of the atmosphere within an internal space through which the exhaust gas is introduced with a predetermined diffusion resistance. The sensing element 20 further includes a pumping cell 44 which is operated to perform an oxygen pumping action for moving oxygen ions into and out of the internal space. The sensor 40 incorporates a control arrangement including an Ip controller for regulating a pumping current Ip to be supplied to the pumping cell 44, such that the electromotive force Vs produced by the sensing cell 42 coincides with a predetermined reference value Vs1. The pumping current Ip regulated in the feedback manner is provided as a non-compensated output $y_0$ of the sensor 40 which generally corresponds to the oxygen concentration of the exhaust gas of the engine 10.

In the feedback control system of the sensor 40 according to the present system, there are incorporated phase advancing elements 52 and 54 for advancing the signal phase of the electromotive force Vs of the pumping cell 42, by respective first-order transfer functions $(1 + t_1 s)$ and $(1 + t_2 s)$.

These phase advancing elements 52, 54 are provided to compensate a transfer lag due to three transfer lag elements 56, 58, 60 which are assumed to exist in the sensing element 20 and which are expressed by the following first-order transfer functions (a), (b) and (c). If the phase advancing elements 52, 54 were not provided, the feedback control system for regulating the pumping current Ip for the pumping cell 44 based on the electromotive force Vs of the sensing cell 42 would tend to oscillate when the system is operated with a relatively high frequency response speed. To avoid this drawback, the phase advancing elements 52, 54 are provided.

(a) Transfer function of the element 56 which represents a transfer lag due to a flow of the exhaust gas from the exhaust pipe 18 into the internal space in the sensing element 20:

$$\left[ \frac{1}{1 + T_3 s} \right] \quad (a)$$

(b) Transfer function of the element 58 which represents a transfer lag due to a flow of the exhaust gas through the internal space from the electrode of the pumping cell 44 to the electrode of the sensing cell 42:

$$\left[ \frac{1}{1 + T_1 s} \right] \quad (b)$$

(c) Transfer function of the element 60 which represents a transfer lag due to diffusion of the exhaust gas through the electrode of the sensing cell 42 in the internal space, to the surface of the solid electrolyte body of the sensing cell:

$$\left[\frac{K}{1+T_2s}\right] \quad (c)$$

In the feedback control system for the pumping current Ip of the pumping cell 44 based on the electromotive force Vs of the sensing cell 42, the transfer function between the Vs and Ip is expressed by a second-order phase retarding transfer function $[1/(1+T_1s)]\cdot[1/(1+T_2s)]$ having two pole points. To compensate the pumping current Ip for the transfer lag represented by the above second-order phase retarding transfer function, the sensor 40 incorporates the phase advancing elements 52, 54 between the sensing cell 42 and the Ip controller 46, for advancing the signal phase of the electromotive force Vs, by a second-order phase advancing transfer function $(1+T_1s)\cdot(1+T_2s)$ which has time constants $t_1$ and $t_2$ corresponding to time constants $T_1$ and $T_2$ in the second-order transfer function. As a result, the feedback control system is protected from otherwise possible oscillation, whereby the control stability of the pumping current Ip is increased.

In the present embodiment, an output $y_0$ of the A/F ratio sensor 40 which corresponds to the oxygen concentration of the exhaust gas (and which is usually represented by the pumping current Ip) is first applied to a temperature compensating portion 48 (FIG. 2B), by which the output $y_0$ is compensated for a variation in the temperature of the sensing element 20.

As described above, the output $y_0$ of the A/F ratio sensor 40 inherently includes an error due to the variation in the temperature Tc of the sensing element 20. In particular, the temperature Tc of the sensing element 20 exposed to the exhaust gas emitted by the internal combustion engine 10 of a motor vehicle considerably changes by several hundreds of °C., due to a change in the running condition of the vehicle. The temperature compensating portion 48 is provided to reduce or eliminate the influence of the variation of the temperature Tc on the output of the sensor 40 as applied to the output device 38.

Described in more detail, the temperature Tc of the sensing element 20 is determined during operation of the sensor 40 to determine the A/F ratio of the air-fuel mixture to be supplied to the engine 10. This determination is possible by actually measuring the temperature of the exhaust gas, and determining the temperature Tc according to a known relationship between the temperature of the exhaust gas and the temperature Tc. This relationship can be obtained by actual measurement of the temperature values Tc at different temperature values of the exhaust gas. In the present embodiment, however, the temperature Tc is obtained by calculation based on actually measured heater voltage $V_H$ and current $I_H$ applied between a heat-generating resistor of a heater provided on the sensing element 20 of the sensor 40. As well known in the art, an electrical resistance $R_H$ of the heat-generating resistor changes with its temperature, so that the temperature Tc can be calculated as a function of a resistance ratio Xt of the resistance $R_H$ to a predetermined reference resistance value $R_{H0}$ (e.g., resistance value of the heat-generating resistor at the room or ambient temperature). This function, which is represented by a functional equation 50 indicated in FIG. 2B is obtained by actual measurement of the temperature values Tc at different ratios Xt.

Figure 2A:
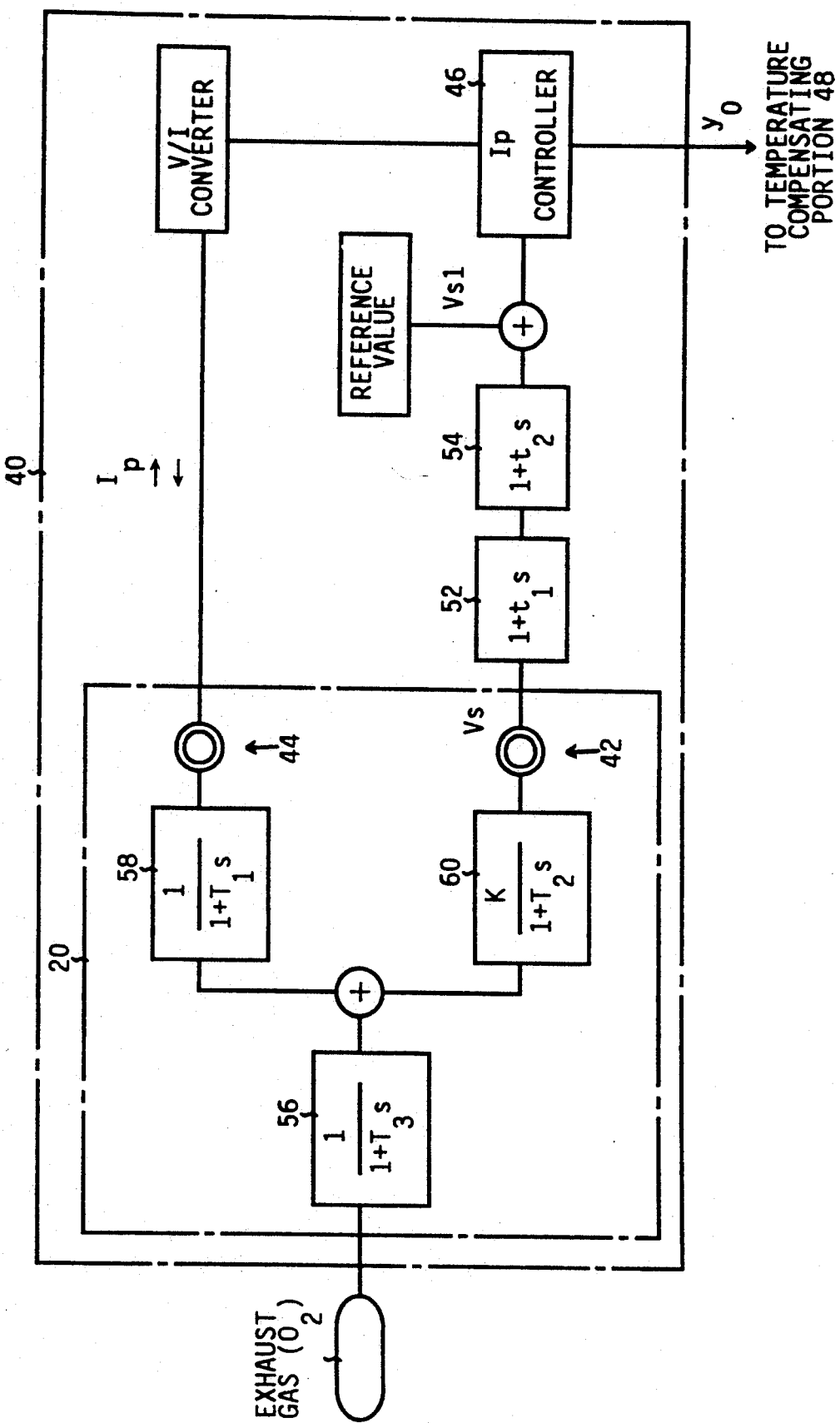
Figure 2B:
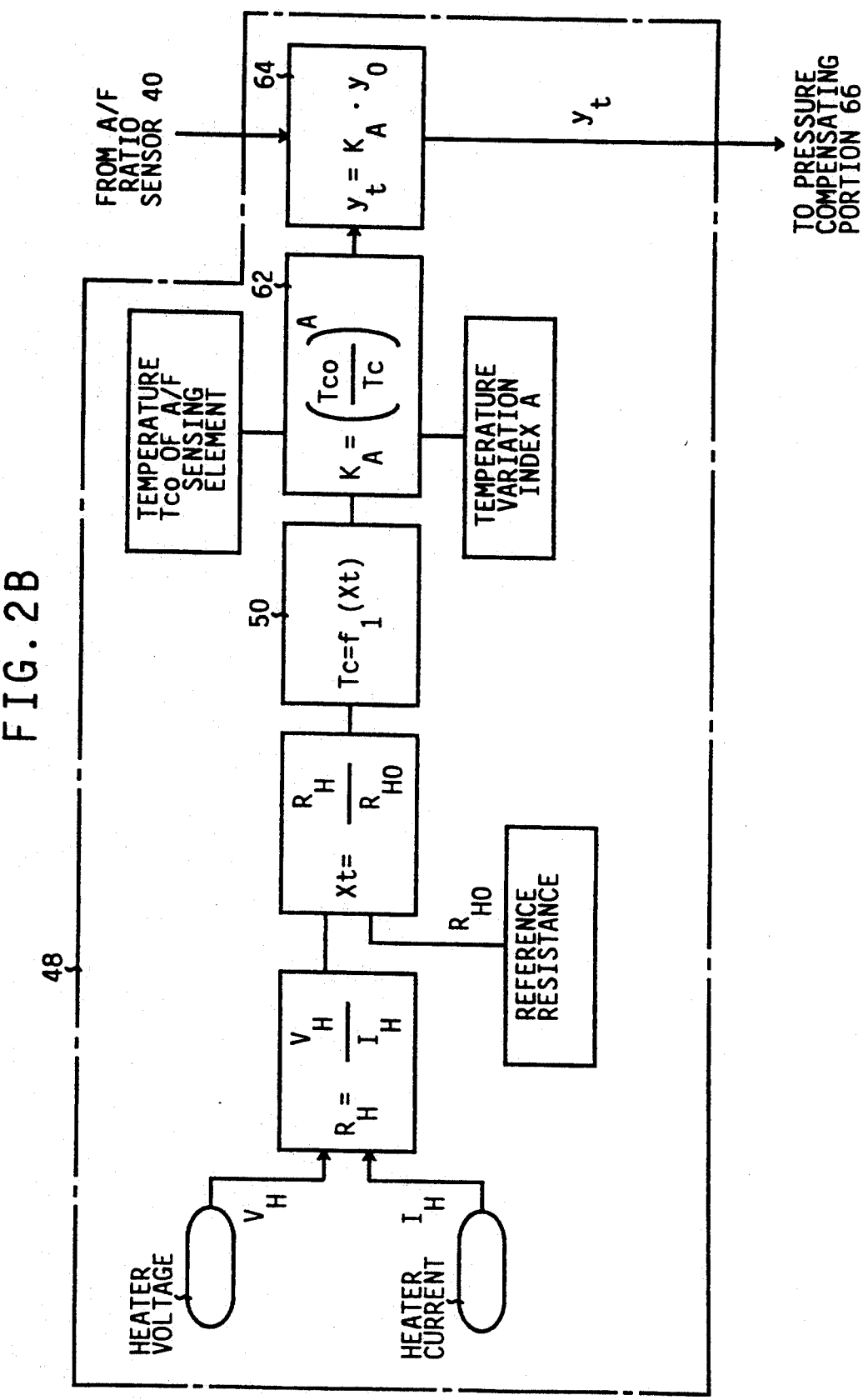

A temperature compensating coefficient $K_A$ is obtained according to the above-indicated formula (1-2) indicated at 62 in FIG. 2B, based on the temperature Tc thus obtained according to the equation 50, a reference temperature Tco of the sensing element 20, and a temperature variation index A of the sensing element 20. The temperature compensating coefficient $K_A$ is used in the above-indicated formula (1—1) indicated at 64 in FIG. 2B, for compensating the output $y_0$ for the variation in the temperature Tc, whereby a temperature-compensated output value $y_t$ of the sensor 40 is obtained.

In the present embodiment, the temperature-compensated output $y_t$ is applied to a pressure compensating portion 66 shown in FIG. 2C, which is adapted to compensate the output $y_t$ for a variation in the pressure Pg of the exhaust gas.

As indicated above, the output $y_0$ of the sensor 40 inherently includes an error due to the variation in the pressure Pg of the exhaust gas. In particular, the volume of the exhaust gas produced by each cylinder 14 of the engine 10 generally changes with a load being exerted on the engine 10, and the pressure Pg of the exhaust gas of the engine 10 changes with the volume of the exhaust gas produced. Namely, the amount of change in the pressure Pg is proportional to a square of the amount of change in the volume of the exhaust gas. While the variation in the pressure Pg changes also with various parameters such as the type of the catalyst 18, pressure loss of the exhaust pipe 16, the pressure Pg inevitably varies by a maximum value of about 450 mmHg under the normal operating conditions of the engine 10. The pressure compensating portion 66 is adapted to compensate the output $y_0$ for this variation in the pressure Pg of the exhaust gas.

More specifically, the pressure Pg of the exhaust gas is determined during operation of the sensor 40. This determination is usually effected by actual measurement of the pressure Pg in the exhaust pipe 16, by the pressure sensing element 22 (FIG. 1). However, the pressure Pg can be calculated by approximation according to an equation 68 (FIG. 2C) based on an operating speed N of the engine 10. In this case, the pressure sensing element 22 can be eliminated. It is noted that Kp in the equation 68 represents a predetermined proportion constant.

Although the pressure Pg measured by the pressure sensing element 22 can be used for compensating the sensor output $y_0$ (temperature-compensated output yt) for the variation in the pressure Pg as described below, the present embodiment is adapted to compensate the measured pressure Pg (output of the pressure sensing element 22) for the following phase differences. That is, there is a phase difference between the output $y_0$ of the sensor 40 and the output Pg of the sensing element 22, due to a difference in the response speeds. Further, there exists a phase difference due to a propagation delay of the pressure Pg, which arises from a distance between the pressure sensing element 22 and the sensing element 20 of the sensor 40, which are spaced from each other along the exhaust pipe 16. The compensation of the pressure Pg for the above phase differences is effected according to the following first-order phase retarding transfer function (d) indicated at 70 in FIG. 2C:

$$\frac{e^{-LS}}{1 + T_6 s} \tag{d}$$

In the above transfer function (d), L represents a time lag (sec.) due to the propagation delay of the pressure Pg between the pressure sensing element 22 and the sensing element 20 of the sensor 40. This value L may be a predetermined constant $L_2$. For improved accuracy of compensation for the variation in the pressure Pg, it is preferable to use a variable $L_1$, which is calculated based on a temperature Tg of the exhaust gas as measured by the temperature sensing element 24, according to the following equations (xii-1) and (xii-2) indicated at 76 in FIG. 2C.

$$L_1 = \frac{\text{distance (m) between elements 20 and 22}}{vt} \tag{vii-1}$$

$$vt = \frac{vo \cdot T_g^{0.5}}{\left[1 - \frac{p}{H} \cdot \left(\frac{\gamma w}{\gamma} - 0.622\right)\right]^{0.5}} \tag{vii-2}$$

where, $vt$: acoustic velocity (m/s) of the exhaust gas at temperature Tg°K, $vo$: acoustic velocity (331 m/s) of the exhaust gas at temperature 0°K, Tg: temperature (°K) of the exhaust gas, p : partial pressure (atm) of water vapor in the exhaust gas, $\gamma w$: constant pressure specific heat of the water vapor, $\gamma$: constant pressure specific heat of the exhaust gas.

In the transfer function (d) indicated above, $T_6$ represents a time constant for compensating the measured pressure Pg for a phase difference which arises from a difference in the response speeds of the sensing element 20 of the sensor 40 and the pressure sensing element 22. The time constant $T_6$ can be approximated by a sum of the time constants $T_1$ and $T_2$ in the transfer functions (b) and (c) described above with respect to the transfer lag elements 58 and 60 of the sensing element 20.

A pressure compensating coefficient $K_B$ is obtained according to the above-indicated formula (3A-3) indicated at in FIG. 2C, based on the pressure Pg thus obtained according to the equation 70 a reference pressure Pgo of the exhaust gas, and a pressure variation index B of the exhaust gas. The pressure compensating coefficient $K_B$ is used in the above-indicated formula (3A-3) indicated at 74 in FIG. 2C, for compensating the output $y_t$ of the temperature compensating portion 48, for the variation in the pressure Pg, whereby a temperature- and pressure-compensated output value $y_{tp}$ of the sensor 40 is By using the thus obtained temperature- and pressure-compensated output ytp of the sensor 40, the relationship among the partial pressures of $O_2$, CO, $H_2$, etc. of the exhaust gas is obtained based on the above equations (iii-1) and (iii-2) which represent the reaction molar numbers before and after the combustion of the air-fuel mixture, and the above equation (iv) which represents the water gas reaction coefficient. In this manner, the oxygen concentration ($\pm O_2\%$) of the exhaust gas, and the excess oxygen ratio $\lambda$ and the A/F ratio of the air-fuel mixture are determined. However, the present embodiment is adapted to compensate the output $y_{tp}$ for a variation in the output among different individuals of the sensor 40 used for the different individuals of the engine 10, before the A/F ratio of the air-fuel mixture is calculated on the basis of the output $y_{tp}$. This compensation is effected by using calibrating equations indicated at 84 and 86 in FIG. 2D, for calibrating the sensor 40. These equations are obtained according to a standard output of the sensor 40 which was measured when a calibrating gas was used as the exhaust gas.

Explained more specifically, the above equation (ii) which represents the relationship between the sensor output Ip (pumping current) and the partial pressures of the $O_2$, CO and $H_2$ components of the exhaust gas can be converted into the following equations (ii'-1), (ii'-2) and (ii'-3):

$$Ip = K_{O2} \cdot \{P_{O2}(II) - i \, KK_{co} \cdot P_{co}\} \tag{ii'-1}$$

$$KK_{co} = K_{co}/K_{O2} \tag{ii'-2}$$

$$KK_{H2} = K_{H2}/K_{O2} \tag{ii'-3}$$

where, $K_{O2}$: current sensitivity coefficient of oxygen concentration, $P_{O2}(II)$: $O_2$ partial pressure of exhaust gas (within the internal space of the sensing element 20, $K_{co}$: current sensitivity coefficient of CO concentration, $P_{co}$: CO partial pressure of exhaust gas, $K_{H2}$: current sensitivity coefficient of H, concentration, and $P_{H2}$: $H_2$ partial pressure of exhaust gas.

The current sensitivity coefficient $K_{O2}$ of the oxygen concentration of each specific individual of the sensor 50 can be obtained by using the calibrating gas whose oxygen concentration is known. The output $y_{tp}$ of the sensor is compensated according to the calibrating equation 84 using a compensating coefficient $K\alpha$ which corresponds to the current sensitivity coefficient $K_{O2}$. Thus, there is obtained a compensated output $y_{tp}'$ of the sensor 40 which is free of an error due to a variation in the current sensitivity of the oxygen concentration of the exhaust gas produced by the fuel-lean air-fuel mixture.

Where the output Ip of the sensor 40 is equal to or larger than zero ("0"), that is, where the air-fuel mixture is a fuel-lean mixture with the excess oxygen ratio $\lambda \geq 1$, the oxygen concentration ($+O_2\%$) of the exhaust gas is calculated by a linearlizer 82, based on the compensated output $y_{tp}'$ obtained according to the equation 84.

Where the output Ip of the sensor 40 is smaller than zero, that is, where the air-fuel mixture is a fuel-rich mixture with the excess oxygen ratio $\lambda < 1$, the above equation (ii) is transformed into the following equations (ii''-1), (ii''-2) and (ii''-3), which uses a compensating coefficient KM:

$$Ip = K_{O2} \cdot \{P_{O2}(II) - KM \cdot (KK_{co} \cdot P_{co} - KK_{H2} \cdot P_{H2})\} \tag{ii''-1}$$

$$KK_{co} = K_{co}/K_{O2} \tag{ii''-2}$$

$$KK_{H2} = K_{H2}/K_{O2} \tag{ii''-3}$$

where, $K_{O2}$: current sensitivity of oxygen concentration, $P_{O_2}(II)$: $O_2$ partial pressure of exhaust gas within internal space of the sensing element 20, KM: compensating coefficient, $K_{CO}$: current sensitivity of CO concentration, $P_{CO}$: CO partial pressure of exhaust gas, $K_{H_2}$: current sensitivity of $H_2$ concentration, and $P_{H_2}$: $H_2$ partial pressure of exhaust gas.

By using the calibrating gas whose CO and $H_2$ concentrations are known, there are obtained the specific coefficient $K_{O_2}$ and compensating coefficient KM of the sensor 40, which provide a compensating coefficient $K\beta = (K_{O_2} \cdot KM)$. This compensating coefficient $K\beta$ is used in the calibrating equation 86 for compensating the output $y_{tp}'$ to obtain a modified output $y_{tp}''$, which is free of an error due to a variation in the current sensitivity of the oxygen concentration of the exhaust gas produced by the fuel-rich air-fuel mixture.

The thus obtained compensated output $y_{tp}''$ for the fuel-rich air-fuel mixture is then applied to a temperature compensating portion 78 which is adapted to compensate the output $y_{tp}''$ for a variation in the temperature Tg of the exhaust gas, according to an equilibrium temperature of the water gas reaction in the exhaust gas.

Namely, the output $y_0$ of the A/F ratio sensor 40 inherently includes an error due to a considerable variation in the equilibrium temperature $T_H$ of the water gas reaction. This variation inevitably occurs because the temperature of the exhaust gas from the engine 10 changes over a wide range between 230° C. and 900° C., depending upon the running condition of the vehicle. The temperature compensating portion 78 is provided to reduce or eliminate the error due to the variation in the equilibrium temperature $T_H$ of the water gas reaction.

In the internal combustion engine 10, the heat of the exhaust gas is absorbed by each cylinder 14 and the corresponding exhaust pipe 16 during transition of the gas from the non-equilibrium state to the semi-equilibrium state. During the suction, compression and expansion strokes of the four operating strokes (suction, compression, expansion and exhaust) of the engine 10, the exhaust gas remains in the exhaust pipe 16 of each cylinder 14. Since the reaction of the water gas progresses in the direction toward the low-temperature side of the exhaust gas, there is a relationship between the temperature Tg of the exhaust gas and the equilibrium temperature $T_H$ of the water gas reaction. Accordingly, the equilibrium temperature $T_H$ can be easily approximated by detecting the temperature Tg of the exhaust gas as described below.

To determine the equilibrium temperature $T_H$, therefore, the temperature Tg of the exhaust gas is measured during operation of the sensor 40, by the temperature sensing element 24 provided in the exhaust pipe 16 (FIG. 1). Since the temperature Tg as measured by the temperature sensing element 24 is considerably lower than the temperature of the exhaust gas as discharged from the cylinder 14, the temperature Tg cannot be directly used as the equilibrium temperature $T_H$.

Figure 2D:
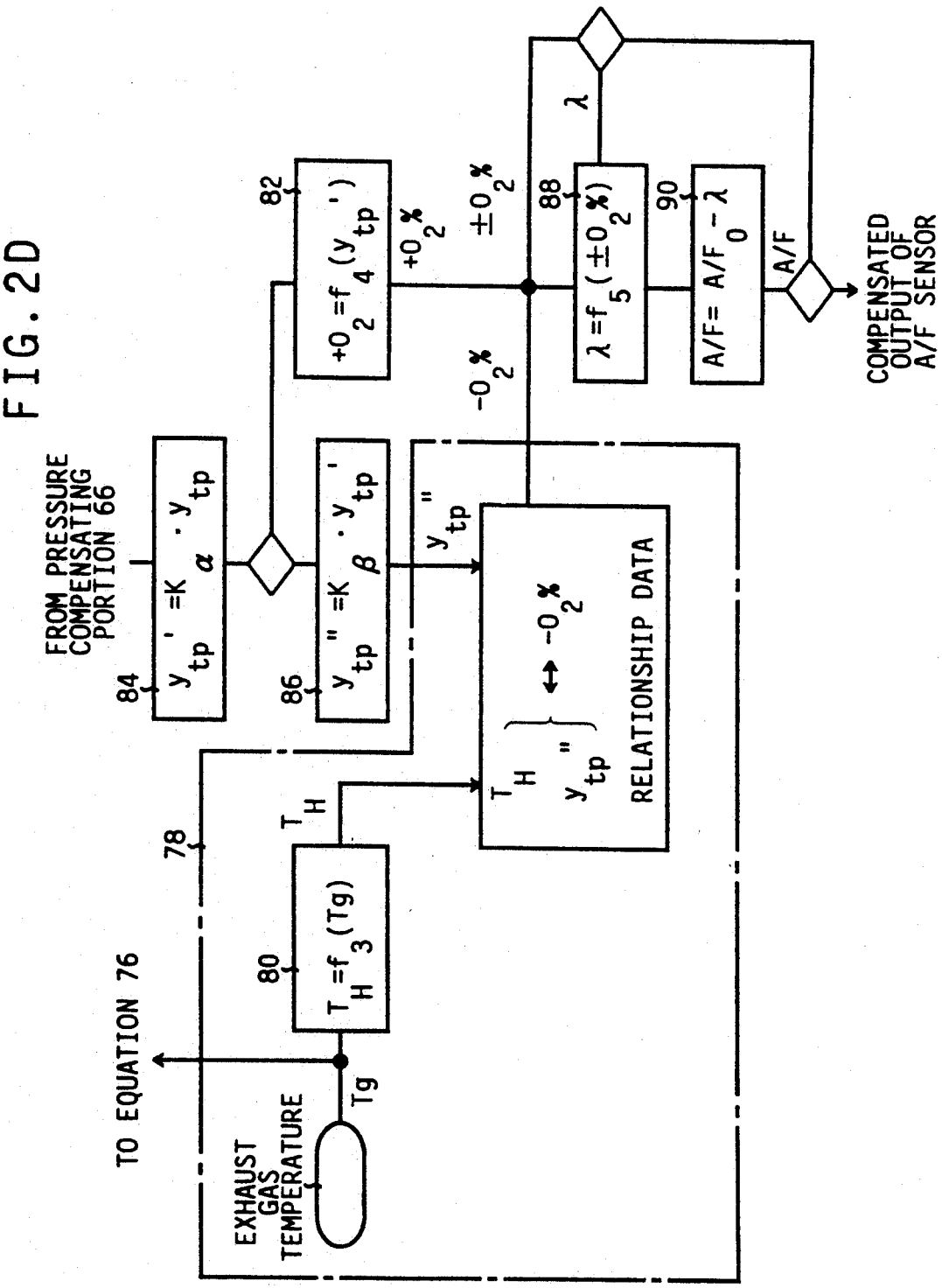

In view of the above difference between the temperature Tg as measured by the sensing element 24 and the equilibrium temperature $T_H$ of the water gas reaction, the relationship between these parameters Tg and $T_H$ is experimentally obtained and represented by an equation 80 indicated in FIG. 2D, in the form of a polynominal or an approximating function, for example. According to this equation 80, the equilibrium temperature $T_H$ is calculated based on the temperature Tg as measured by the temperature sensing element 24.

By using the equilibrium temperature $T_H$ of the water gas reaction, the relationship between the compensated output $y_{tp}''$ of the sensor 40 and the $O_2$, CO and $H_2$ partial pressures of the exhaust gas is obtained according to the above equations (iii-1) and (iii-2) which represent the reaction molar numbers before and after the combustion of the air-fuel mixture, and the above equation (iv) which represents the water gas reaction coefficient. In this manner, there is calculated the oxygen concentration ($-O_2\%$) of the exhaust gas, which is free or almost free of the error due to the variation in the temperature Tg of the exhaust gas, as well as the errors due to the variations in the temperature Tc of the sensing element 20 and the pressure Pg of the exhaust gas.

The oxygen concentration ($-O_2\%$) of the exhaust gas can be calculated directly from the above equations (iii-1), (iii-2) and (iv), based on the equilibrium temperature $T_H$ and the compensated output $y_{tp}''$. For the internal combustion engine 10 for a motor vehicle wherein the A/F ratio of the air-fuel mixture is required to be controlled with a high response, it is desirable that a calculation table representative of the relationship among the parameters $T_H$, $y_{tp}''$ and $-O_2\%$ be prepared to calculate the $-O_2\%$ by interpolation.

TABLE 3 shows an example of the calculation table representative of the relationship among the parameters $T_H$, compensated output $y_{tp}''$ and $-O_2\% = (H_2 + CO)/2$, where the molar ratio H/C of hydrogen and carbon of the air-fuel mixture is 1.85 while the molar ratio O/C of oxygen and carbon of the mixture is zero. This relationship is prepared according to the equations (iii-1), (iii-2) and (iv). The oxygen concentration $-O_2\%$ of the exhaust gas is calculated by interpolation of the values in the calculation table, based on the equilibrium temperature $T_H$ obtained from the actually measured temperature Tg of the exhaust gas, and on the compensated output $y_{tp}''$ of the sensor 40 calculated according to the equation 86 described above.

TABLE 3

| | | Sensor Output $y_{tp}''$ (mA) | | | | | |
| | | Equilibrium Temp. $T_H$ (°C.) of Water Gas Reaction | | | | | |
| $-O_2\%$ | λ | 750 | 950 | 1150 | 1350 | 1550 | 1700 |
|---|---|---|---|---|---|---|---|
| −15.59 | 0.50 | −14.89 | −14.13 | −13.60 | −13.23 | −12.96 | −12.80 |
| −11.16 | 0.60 | −10.80 | −9.91 | −9.29 | −8.84 | −8.50 | −8.31 |
| −7.57 | 0.70 | −7.42 | −6.59 | −6.01 | −5.58 | −5.27 | −5.08 |
| −4.61 | 0.80 | −4.58 | −3.93 | −3.48 | 3.17 | −2.94 | −2.31 |
| −2.12 | 0.90 | −3.31 | −1.77 | −1.53 | −1.36 | −1.25 | −1.19 |
| 0.00 | 1.00 | −0.00 | −0.00 | −0.00 | −0.00 | −0.00 | −0.00 |
| | | (H/C = 1.85, O/C = 0) | | | | | |

In the present embodiment, the oxygen concentration ($\pm O_2\%$) of the exhaust gas is obtained from the compensated outputs $y_{tp}'$ and $y_{tp}''$ of the A/F ratio sensor 40. If other data such as the excess air ratio (λ) and A/F ratio of the air-fuel mixture are desired, these values are calculated according to respective equations indicated at 88 and 90 in FIG. 2D. For example, the excess air ratios (λ) of the fuel-lean and fuel-rich air-fuel mixtures are calculated from the oxygen concentration (±O₂%), according to the following equations (xiii-1) and (xiii-2):

(1) In the case of +O₂% of fuel-lean air-fuel mixture $$\lambda = \frac{20.95}{(20.95 - O_2)} \cdot \left(1 + \frac{O_2}{100} \cdot \frac{n}{4} \cdot \frac{1}{(m + n/4)}\right) \quad \text{(xiii-1)}$$

(2) In the case of −O₂% of fuel-rich air-fuel mixture:

$$\lambda = \frac{20.95}{(20.95 - 0.7905 \cdot O_2)} \cdot \left[1 + \frac{O_2}{100} \cdot \left(1 + \left(\frac{n}{4} \cdot \frac{1}{(m + n/4)}\right)\right)\right] \quad \text{(xiii-2)}$$

where,

O₂: oxygen concentration obtained from the sensor output ($y_{tp}'$ or $y_{tp}''$), n: molar number of carbon component in 1 mole of the fuel, and m: molar number of hydrogen component in 1 mole of the fuel.

It will be understood from the foregoing description that the present embodiment of the invention is adapted to compensate the output $y_0$ for the variations in the temperature Tc of the sensing element 20 of the sensor 40 and in the pressure Pg of the exhaust gas, whereby the compensated output values $y_{tp}'$ and $y_{tp}''$ are obtained. Where the air-fuel mixture is a fuel-rich mixture, the compensated output $y_{tp}''$ is further compensated for the variation in the temperature Tg of the exhaust gas. Based on the compensated output values $y_{tp}'$ and $y_{tp}''$, the air/fuel ratio of the air-fuel mixture and other parameters associated with the mixture can be accurately determined, according to the present method, which effectively eliminates or minimizes the errors which are conventionally included in the sensor output due to the variations in the temperature of the sensing element 20 and the pressure and temperature of the exhaust gas. In other words, the illustrated method of compensating the output of the A/F ratio sensor 40 assures accurate and optimum regulation of the air/fuel ratio of the air-fuel mixture to be supplied to the internal combustion engine 10, based on the accurate determination of the actual air-fuel ratio.

While the present invention has been described in detail in its presently preferred embodiment for illustrative purpose only, it is to be understood that the invention is not limited to the details of the illustrated embodiment, but may be embodied with various changes, modifications and improvements, which may occur to those skilled in the art, without departing from the spirit of the invention in the light of the foregoing teaching.

In the illustrated embodiment, the phase advancing elements 52, 54 are provided in the A/F ratio sensor 40 to eliminate a transfer lag in the feedback control system for the pumping current. However, these elements 52, 54 are not essential to practice the principle of the present invention.

While the illustrated embodiment is adapted to successively compensate the output of the sensor 40 for a variation in the temperature of the sensing element 20, a variation in the pressure of the exhaust gas, and a variation in the temperature of the exhaust gas, the output of the sensor 40 may be compensated for one or two of the variations of the above-indicated three parameters. In this case, too, the object of the present invention of improving the accuracy of the sensor output is achieved with an appreciable effect.

In the illustrated embodiment wherein the pressure sensing element 22 is disposed nearer to the engine 10 than the sensing element 20 of the sensor 20, the phase retarding transfer function element 70 is provided to eliminate a phase difference between the outputs of the sensor 40 and the sensing element 22, due to a propagation delay of the measured pressure Pg with respect to the sensor output, which delay arises from a distance between the pressure sensing element 22 and the sensing element 20. If the sensing element 20 is disposed nearer to the engine 10 than the pressure sensing element 22, the phase difference is reversed, and the element 70 should be replaced by a transfer function of $e^{-LS}$.

However, the compensation of the sensor output for the phase difference due to the distance between the sensing elements 20, 22, and the compensation for a difference in the operating response of the two sensing elements 20, 22 are not essential according to the present invention.

In the illustrated embodiment, the temperature compensating coefficient $K_A$ and the pressure compensating coefficient $K_B$, and the compensated outputs $y_t$ and $y_{tp}$ based on these coefficients are obtained by calculation. However, the coefficients $K_A$, $K_B$ and the compensated outputs $y_t$, $y_{tp}$ can be obtained by interpolation using prepared data tables representative of relationships among the output $y_0$ as produced by the sensor 40, temperature and pressure variation indices A and B, and compensated outputs $y_t$ and $y_{tp}$.

While the illustrated embodiment is applied to the A/F ratio sensor using the double-cell type oxygen sensor having the sensing and pumping cells 42, 44, the principle of the invention is equally effectively applicable to an A/F ratio sensor using a single-cell type oxygen sensor, which is usually an oxygen concentration cell. In this case, the output y of the A/F ratio sensor is obtained in the form of an electromotive force (EMF), and is compensated for a variation in the temperature of the sensing element, according to the formulas (1—1) and (1-2) indicated above, and for a variation in the pressure of the exhaust gas, according to the formulas (2B-1) and (2B-2). As in the case of the double-cell type A/F ratio sensor, the oxygen concentration (±O₂%) excess air ratio (λ) and A/F ratio can be readily and efficiently determined based on the sensor output in the form of the electromotive force (EMF), depending upon the reaction molar numbers before and after the combustion of the air-fuel mixture and the water gas reaction coefficient, with the molar ratios of H/C and 0/C of the air-fuel mixture being suitably predetermined.

It will be understood that the principle of the present invention is effectively applicable to a sensor for determining the air/fuel ratio of an air-fuel mixture to be supplied to equipment other than an automotive vehicle engine.

What is claimed is:

1. A method of compensating an output of a sensor adapted to determine and air/fuel ratio of an air-fuel mixture, depending upon an oxygen concentration of an exhaust gas produced as a result of combustion of the air-fuel mixture, said sensor including a sensing element which has at least one electrochemical cell each having an oxygen-conductive solid electrolyte body and at least one pair of electrodes, said method comprising the steps of:

detecting a temperature Tc of said sensing element; and adjusting the output $y_0$ of said sensor according to the following formulas (1—1) and (1-2), to obtain a compensated output $y_t$ of said sensor:

$$y_t = K_A \quad (1\text{—}1)$$

$$K_A = (Tco/Tc)^A \quad (1\text{-}2)$$

wherein

Tco: reference temperature of said sensing element, and

A: temperature variation index measured at said sensing element.

2. A method of compensating an output of a sensor adapted to determine an air/fuel ratio of an air-fuel mixture, depending upon an oxygen concentration of an exhaust gas produced as a result of combustion of the air-fuel mixture, said sensor including a sensing element having a first and a second electrochemical cell and an internal space formed therebetween, said first electrochemical cell being operable according to the principle of an oxygen concentration cell, so as to produce an electromotive force corresponding to an oxygen partial pressure of an atmosphere in said internal space into which said exhaust gas diffuses with a predetermined diffusion resistance, said second electrochemical cell operating to perform an oxygen pumping action to adjust the oxygen partial pressure in said internal space so that said electromotive force substantially coincides with a constant value, said output of the sensor being obtained as a pumping current applied to said second electrochemical cell, said method comprising the steps of:

detecting a pressure Pg of said exhaust gas;

adjusting the output $y_0$ of said sensor, according to the following formulas (2A-1) and (2A-2), to obtain a compensated output $y_p$ of said sensor:

$$y_p = y_0 \times K_B \quad (2A\text{-}1)$$

$$K_B = (Pgo/Pg)^B \quad (2A\text{-}2)$$

wherein

Pgo: reference pressure of said exhaust gas, and

B: variation index of the exhaust gas pressure measured for said sensing element.

3. A method of compensating an output of a sensor adapted to determine an air/fuel ratio of an air-fuel mixture, depending upon an oxygen concentration of an exhaust gas produced as a result of combustion of the air-fuel mixture, said sensor including a sensing element which has a single electrochemical cell having an oxygen-conductive solid electrolyte body and at least one pair of electrodes, and said output of said sensor is obtained as an electromotive force induced by said single electrochemical cell, said method comprising the steps of:

detecting a pressure Pg of said exhaust gas; and adjusting the output $y_o$ of said sensor according to the following formulas (2B-1) and 2B-2), to obtain a compensated output $y_p$ of said sensor:

$$y_p = y_0 - K_B' \quad (2B\text{-}1)$$

$$K_B' = \left(\frac{RTc}{4F}\right) \cdot \log(Pgo/Pg) \quad (2B\text{-}2)$$

wherein

R: gas constant,

F: Faraday constant, and

Pgo: reference pressure of said exhaust gas.

4. A method of compensating an output of a sensor adapted to determine an air/fuel ratio of an air-fuel mixture, depending upon an oxygen concentration of an exhaust gas produced as a result of combustion of the air-fuel mixture, said sensor including a sensing element which has a first and a second electrochemical cell and an internal space formed therebetween, said first electrochemical cell being operable according to the principle of an oxygen concentration cell, so as to produce an electromotive force corresponding to an oxygen partial pressure of an atmosphere in said internal space into which said exhaust gas diffuses with a predetermined diffusion resistance, said second electrochemical cell operating to perform an oxygen pumping action to adjust the oxygen partial pressure in said internal space so that said electromotive force substantially coincides with a constant value, said output of the sensor being obtained as a pumping current applied to said second electrochemical cell, said method comprising the steps of:

detecting a temperature Tc of said sensing element and a pressure Pg of said exhaust gas; and adjusting the output $y_0$ of said sensor according to the following formulas (3A-1), 3A-2) and (3A-3), to obtain a compensated output $y_{tp}$ of said sensor:

$$y_{tp} = y_0 \times K_A \times K_B \quad (3A\text{-}1)$$

$$K_A = (Tco/Tc)^A \quad (3A\text{-}2)$$

$$K_B = (Pgo/Pg)^B \quad (3A\text{-}3)$$

wherein

Tc$_0$: reference temperature of said A/F sensing element,

A: temperature variation index measured at said sensing element;

Pgo: reference pressure of said exhaust gas, and

B: variation index of the exhaust gas pressure measured for said sensing element.

5. A method of compensating an output of a sensor adapted to determined an air/fuel ratio of an air-fuel mixture, depending upon an oxygen concentration of an exhaust gas produced as a result of combustion of the air-fuel mixture, said sensor including a sensing element which has a single electrochemical cell having an oxygen-conductive solid electrolyte body and at least one pair of electrodes, and said output of said sensor is obtained as an electromotive force induced by said single electrochemical cell, said method comprising the steps of:

detecting a temperature Tc of said sensing element and a pressure Pg of said exhaust gas; and adjusting the output $y_0$ of said sensor according to the following formulas (3B-1), 3B-2) and (3B-3), to obtain a compensated output $y_{tp}$ of said sensor:

$$y_{tp} = (y_0 - K_B') \cdot K_A \quad \text{(3B-1)}$$

$$K_A = (T_{co}/T_c)^A \quad \text{(3B-2)}$$

$$K_B' = \left(\frac{RT_c}{4F}\right) \cdot \log(P_{go}/P_g) \quad \text{(3B-3)}$$

wherein

A: temperature variation index ($=1$) of said sensing element,

Tco: reference temperature of said sensing element,

R: gas content,

F: Faraday constant, and

Pgo: reference pressure of said exhaust gas.

6. A method of compensating an output of a sensor adapted to determine an air/fuel ratio of an air-fuel mixture, depending upon an oxygen concentration of an exhaust gas produced as a result of combustion of the air-fuel mixture, said sensor including a sensing element which has at least one electrochemical cell each having an oxygen-conductive solid electrolyte body and at least one pair of electrodes, said method comprising the steps of:

detecting at least one parameter selected from the group consisting of a temperature Tc of said sensing element, a pressure Pg of said exhaust gas, and a temperature Tg of said exhaust gas;

adjusting the output $y_0$ of said sensor, based on said at least one parameter detected, to obtain a compensated output of said sensor; and determining whether or not the output of said sensor represents the air/fuel ratio lower than a stoichiometric point, and wherein said step of detecting at least one parameter consists of detecting said temperature Tg of said exhaust gas if an affirmative decision is obtained in said determining step, and said step of adjusting the output of said sensor consists of calculating by approximation of equilibrium temperature $T_H$ of a water gas which gives an equilibrium of reaction of said exhaust gas, based on said temperature Tg of said exhaust gas, according to an experimentally obtained approximating formula, and compensating the output of said sensor so as to establish the equilibrium of reaction of said water gas at said equilibrium temperature $T_H$.

* * * * *